United States Patent
Seibold et al.

(10) Patent No.: US 9,216,100 B2
(45) Date of Patent: Dec. 22, 2015

(54) MEDICAL DEVICE

(75) Inventors: Jürgen Seibold, Ludwigsburg (DE);
Erhard Müller, Stuttgart (DE); Karel Volenec, Hradec Králové (CZ); Petr Sittner, Prague (CZ); Ludek Heller, Karlovy Vary (CZ); Jan Pilch, Klecany (CZ)

(73) Assignee: Deutsche Institute für Textil-und Faserforschung Denkendorf Stiftung des öffentlichen Rechts (DE)

( * ) Notice: Subject to any disclaimer, the term of this patent is extended or adjusted under 35 U.S.C. 154(b) by 176 days.

(21) Appl. No.: 13/375,261

(22) PCT Filed: May 30, 2009

(86) PCT No.: PCT/EP2009/003899
§ 371 (c)(1),
(2), (4) Date: Jan. 24, 2012

(87) PCT Pub. No.: WO2010/139340
PCT Pub. Date: Dec. 9, 2010

(65) Prior Publication Data
US 2012/0116492 A1    May 10, 2012

(51) Int. Cl.
*A61F 2/06* (2013.01)
*A61F 2/90* (2013.01)
(Continued)

(52) U.S. Cl.
CPC ... *A61F 2/90* (2013.01); *A61F 2/07* (2013.01); *A61L 31/022* (2013.01); *A61L 31/10* (2013.01); *A61L 31/14* (2013.01); *D02G 3/36* (2013.01); *D02G 3/448* (2013.01); *D03D 3/02* (2013.01); *D03D 13/004* (2013.01); *D03D 13/008* (2013.01); *D03D 15/0027* (2013.01); *D03D 15/0077* (2013.01); *D03D 27/00* (2013.01); *A61F 2/06* (2013.01); *A61F 2002/075* (2013.01); *A61L 2400/16* (2013.01);
(Continued)

(58) Field of Classification Search
CPC ..... A61F 2/07; A61F 2210/0014; A61F 2/06; A61F 2/90; A61F 2002/30014
USPC ........... 623/1.11, 1.13, 1.15, 1.39, 1.49–1.54; 606/108, 191, 194, 198, 200; 442/199, 442/200, 311; 600/32
See application file for complete search history.

(56) References Cited

U.S. PATENT DOCUMENTS 4,892,539 A * 1/1990 Koch .......................... 623/1.52
5,545,212 A * 8/1996 Wakabayashi et al. ...... 623/1.49
(Continued)

FOREIGN PATENT DOCUMENTS

WO       03/088872 A1    10/2003
WO    2008/112242 A2    9/2008

OTHER PUBLICATIONS

"Shape Memory Polymers & their applications." The Indian Textile Journal. Jan. 15, 2008.*
(Continued)

*Primary Examiner* — Katherine M Shi
(74) *Attorney, Agent, or Firm* — DLA Piper LLP (US)

(57) ABSTRACT

A medical device includes yarns made of a shape memory material and polymer yarns, wherein the yarns made of said shape memory material include polymer sheathing.

33 Claims, 3 Drawing Sheets

(51) Int. Cl.
   *A61F 2/07*    (2013.01)
   *A61L 31/02*   (2006.01)
   *A61L 31/10*   (2006.01)
   *A61L 31/14*   (2006.01)
   *D02G 3/36*    (2006.01)
   *D02G 3/44*    (2006.01)
   *D03D 3/02*    (2006.01)
   *D03D 13/00*   (2006.01)
   *D03D 15/00*   (2006.01)
   *D03D 27/00*   (2006.01)

(52) U.S. Cl.
   CPC ...... *C08L 2201/12* (2013.01); *D10B 2401/046* (2013.01); *D10B 2509/06* (2013.01)

(56) References Cited

U.S. PATENT DOCUMENTS

| | | | |
|---|---|---|---|
| 5,928,280 A * | 7/1999 | Hansen et al. | 623/1.15 |
| 6,652,574 B1 | 11/2003 | Jayaraman | |
| 7,063,721 B2 * | 6/2006 | Takahashi et al. | 623/1.51 |
| 2001/0000188 A1 | 4/2001 | Lenker et al. | |
| 2003/0055488 A1 * | 3/2003 | Igaki | 623/1.15 |
| 2003/0078650 A1 * | 4/2003 | Nunez et al. | 623/1.51 |
| 2003/0171053 A1 * | 9/2003 | Sanders | 442/340 |
| 2004/0162606 A1 | 8/2004 | Thompson | |
| 2005/0288775 A1 * | 12/2005 | Dong | 623/1.54 |
| 2008/0228028 A1 * | 9/2008 | Carlson et al. | 600/36 |
| 2009/0099652 A1 * | 4/2009 | Granada et al. | 623/1.46 |
| 2010/0268327 A1 | 10/2010 | Bruszewski et al. | |
| 2010/0305687 A1 * | 12/2010 | Ajji et al. | 623/1.41 |

OTHER PUBLICATIONS

Corresponding European Search Report dated Apr. 13, 2015 of European Application No. 09776667.9.

* cited by examiner

MEDICAL DEVICE

RELATED APPLICATION

This is a §371 of International Application No. PCT/EP2009/003899, with an international filing date of May 30, 2009 (WO 2010/139340 A1, published Dec. 9, 2010), the subject matter of which is incorporated by reference.

TECHNICAL FIELD

This disclosure relates to a medical device, a delivery system for the device, a method for the production of the device, a method using the device as well as use of the device in the field of surgery.

BACKGROUND

Generally, tubular or hose-type medical devices, so-called "stents," are employed as endoprostheses for the treatment of dysfunctions of hollow spaces or cavities in a living organism. Stents usually comprise a wire cage and are intended as a guide rail type reinforcement or support of hollow bodies in humans or animals. Typical fields of application include a vascular system, a gastrointestinal system, and a urinary system, for example. Usually, stents are applied in a compressed condition with the aid of a suitable delivery instrument, like a catheter or a trocar, for example, through the hollow body to be treated up to the intended treatment site and released there. Deployment of the stent provided in a compressed state in the delivery instrument is effected by inherent spring reset forces, due to the stent design principle, or by means of balloon dilatation. What is essential is that the stents will endure dynamic and static deformation over a long time without suffering appreciable loss of their original restoring forces. An ideal case prerequisite is that the stent will conform to the place of application relative to a lumen of the human or animal hollow body to be treated as well as relative to flexibility of the treated region and will remain in the living body as a permanent device.

An example of the above-described stents relates to so-called "stent-grafts." A stent-graft is a tubular device composed of a special fabric supported by the rigid structure of a stent. Stent-grafts are typically configured by separately forming the graft and the stents, and then attaching the graft to the stents. To attach a stent to a graft, the graft is typically inserted into, or pulled over the stent, and the graft is sewn to the structural components of the stent. Alter-natively, the stent may be formed on the graft such that by way of example the individual wires of the stent are threaded through specially provided projecting fabric loops on the surface of the graft, thereby facilitating attachment of the graft to the stent.

However, attachment of the graft to the stent in the above described ways may often result in an undesired bulk requiring a delivery system of a large diameter. Further, attachment of the graft to the stent, normally by sewing, may provide potential sites for undesirable leakage of body fluids, in particular blood, through the graft structure. A further disadvantage relates to the interior wall of these stent grafts. Due to the stent wires projecting from the fabric of the graft, the interior wall is usually not smooth, but profiled. Due to the profile of the interior wall, adherence of blood components may occur to the inner wall of the stent-graft, thereby increasing the risk of forming a thrombosis and subsequent restenosis.

WO 2008/112242 A2 discloses a stent-graft based on a Nitinol wire and textile strands. For the production of such a stent-graft, the Nitinol wire is first shape set into a required shape. Then, such shape set Nitinol wire is processed together with the textile strands to obtain the stent-graft. This approach is probably employed since process engineering of the stent-graft under high temperatures (the conventional heat treatment of Nitinol is performed at temperatures between 560 and 580° C.) is complicated. In particular, the usage of numerous potentially qualified fiber materials is precluded by such elevated temperatures. Another withdrawal relates to a reduced adhesion among the Nitinol wire and the textile strands resulting in an increased displacement mobility between the Nitinol wire and the textile strands leading to an increased risk for leakage to occur during use of such a stent-graft.

It could therefore be helpful to provide an improved medical device to overcome the shortcomings of conventional stents or stent-grafts, in particular in relation to leakage, interior profile, the occurrence of thrombosis or restenosis, equally capable of enduring dynamic and static deformations over a long time, without appreciable loss of its original radial expansive pressure. Furthermore, the medical device should be produced in a most simple way and applied medically under gentle conditions.

SUMMARY

We provide a medical device including yarns made of a shape memory material and polymer yarns, wherein the yarns made of the shape memory material include polymer sheathing.

We also provide a delivery system including the medical device and a delivery instrument.

We further provide a method for producing the medical device, wherein the medical device including yarns made of a shape memory material including polymer sheathing and polymer yarns is subject to a thermal shape setting procedure.

We further yet provide a medical device obtainable according to the method.

We also further provide a method of using the medical device, including percutaneously or orificially placing the device within a body lumen.

BRIEF DESCRIPTION OF THE DRAWINGS

As shown in FIG. 2, the sheathed shape memory material yarns are arranged in the weft direction and the polymer yarns are arranged in the warp direction.

DETAILED DESCRIPTION

Figure 1:
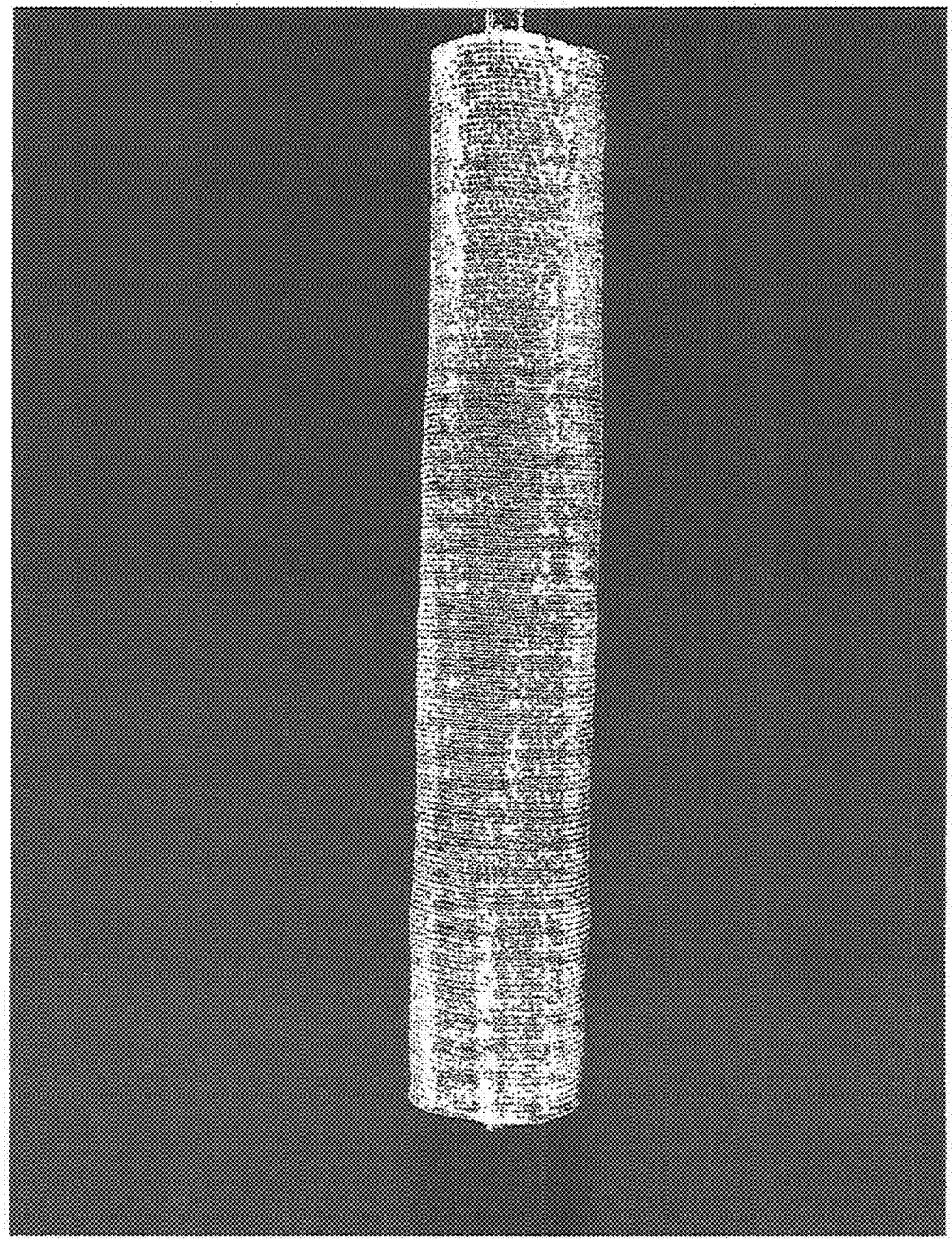
FIG. 1 is a photograph of a medical device designed as endoluminal graft material.
Figure 2:
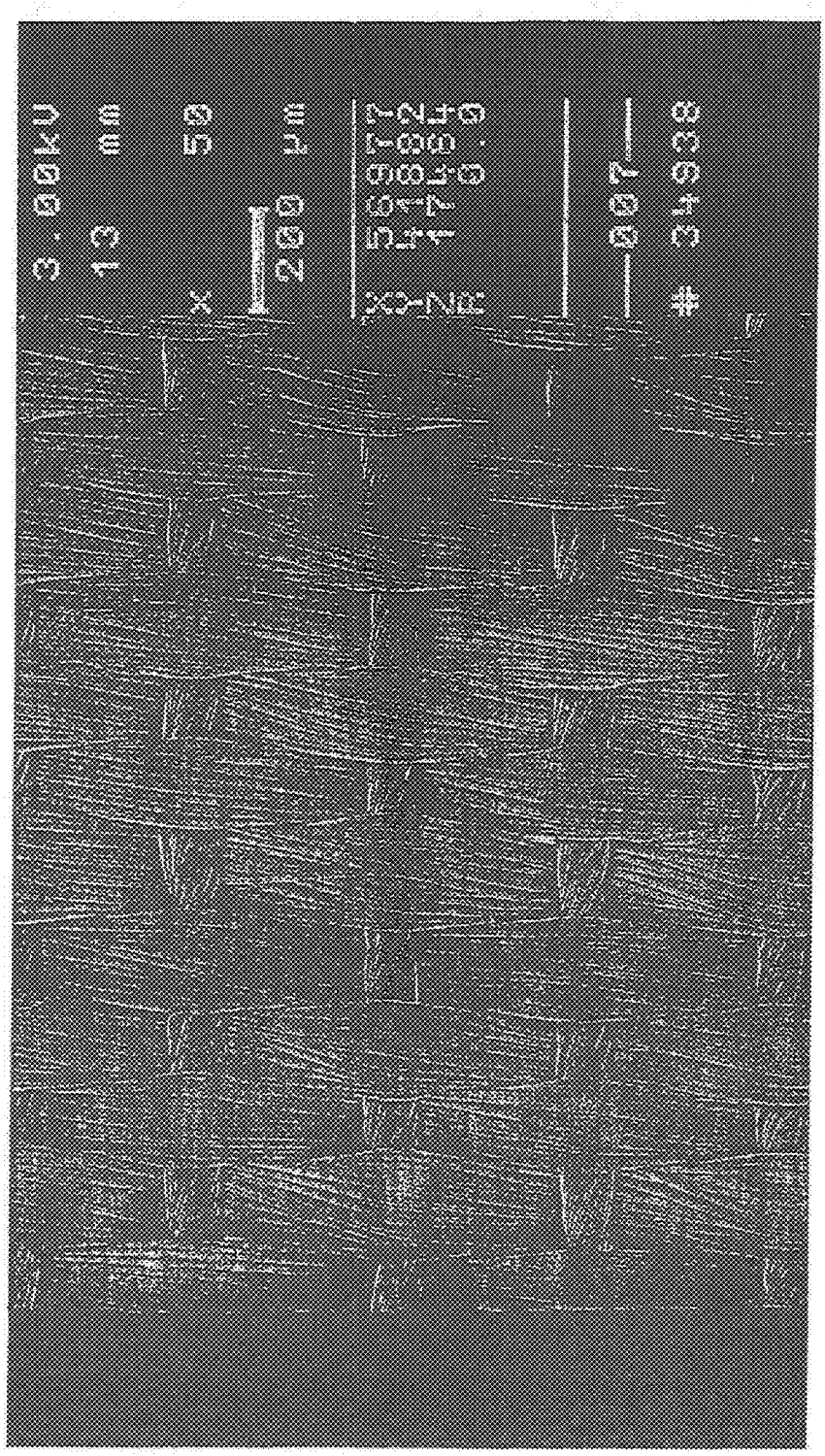
FIG. 2 displays a photographic section of a plain weave as a possible textile pattern in which the sheathed shape memory material yarns and the polymer yarns may be arranged.

We provide a medical device comprising yarns made of a shape memory material and comprising polymer yarns, wherein the yarns made of the shape memory material preferably comprise a polymer sheathing or casing.

The term "yarns made of a shape memory material" as used herein relates to yarns that basically consist of a shape memory material. However, it is within the scope of this disclosure that the yarns may comprise a minor amount of another material in particular additives, ingredients or the like, without affecting the shape memory properties of the shape memory material.

The term "yarns" as used herein is a generic term for a continuous yarn of material suitable for textile processing. For instance, yarns may include fibers, monofilaments, pseudo-monofilament, multifilaments, threads, strands, strings, monofilament yarns, multifilament yarns, spun-type yarns, roving yarns, crepe yarns, ply yarns, cord yarns, wires or combinations thereof.

The term "sheathed shape memory material yarns" as used herein is equivalent to the term "yarns made of a shape memory material comprising a polymer sheathing or casing."

Surprisingly, it turned out that our device is less prone to an undesired leakage of body fluids which is mainly due to the sheathing of the yarns made of the shape memory material. The sheathing or casing contributes to an increased resistance to displacement of the sheathed shape memory material yarns and the polymer yarns. In other words, adhesion between the sheathed shape memory material yarns and the polymer yarns is improved, whereby a risk of leakages in the device may be prevented or at least considerably reduced.

Generally, the polymer sheathing may only partially surround the yarns made of the shape memory material. Preferably, the polymer sheathing completely surrounds the yarns made of the shape memory material, in particular all over the surface.

Particularly preferably, the polymer sheathing is formed as a textile sheathing. Particularly, the polymer sheathing is arranged in the form of fibers, monofilaments, pseudo-monofilament, multifilaments, threads, strands, strings, monofilament yarns, multifilament yarns, spun-type yarns, roving yarns, crepe yarns, ply yarns, cord yarns, wires or combinations thereof. A textile sheathing arranged in the form of monofilaments and/or multifilaments, in particular monofilament yarns and/or multifilament yarns is preferred. The textile sheathing may be arranged to enwind, wrap or plait around the yarns made of the shape memory material.

Preferably, the polymer sheathing is arranged in the form of a coating. In other words, the yarns made of the shape memory material may be designed as coated yarns. For instance, dipping or spraying techniques may be applied to design the coated yarns. Particularly preferred is that the yarns made of the shape memory material and the polymer sheathing are arranged in the form of yarns having a core-sheath structure, wherein the core is formed by the yarns made of the shape memory material and the sheath is formed by the polymer sheathing. Such yarns may be obtained by a bicomponent extrusion procedure or a sheath extrusion procedure, for example. By sheath extrusion, the sheathed shape memory material yarns may be also designed as pseudo-monofilaments.

Further preferably, the medical device is provided in a thermally set condition. In other words, the device preferably has a shape formed by a thermosetting or thermal shape-setting treatment, in particular at an environmental temperature 250° C. This kind of thermosetting procedure may be denoted as "low temperature shape setting treatment" because it is usually performed at an environmental temperature being distinctly below 500° C. (at or above which conventional heat treatment of Nitinol shape memory alloy is commonly carried out). In addition to setting the shape of the device, this treatment can be employed to modify the erectability and elasticity of the sheathed shape memory material yarns and/or the polymer yarns as desired for particular application. Thus, the sheathed shape memory material yarns may have a modulus of elasticity (Young's modulus) from 20 to 80 N/mm2, preferably from 50 to 70 N/mm2. The Young's modulus of the polymer yarns may be from 300 to 1500 cN/tex, in particular from 500 to 1000 cN/tex. The modification of the shape and properties of the sheathed shape memory material yarns and/or the polymer yarns result advantageously in an overall improved spring reset force of the device. The device may have a restoring force, preferably a radial expansive pressure, from 0.2 to 30 kPa, preferably from 0.5 to 5 kPa.

The polymer sheathing may further have a proportion of 10 to 90% by weight, preferably 30 to 70% by weight, based on the total weight of the sheathed shape memory material yarns.

Basically, the shape memory material may be selected from the group consisting of a shape memory polymer, a shape memory metal, a shape memory alloy, and combinations thereof. In particular, the yarns made of the shape memory material comprise shape memory metal wires, shape memory alloy wires or combinations thereof. Furthermore, the yarns made of the shape memory material may be formed from one (single) shape memory metal wire or one (single) shape memory alloy wire. It is, in particular, within the scope of this disclosure that the yarns made of the shape memory material are designed as one (single) shape memory metal wire or one (single) shape memory alloy wire. Shape memory alloys are preferred. Suitable shape memory alloys are selected from the group consisting of nickel-titanium alloy (Nitinol), copper-zinc alloy (CuZn), copper-zinc-aluminium alloy (CuZnAl), copper-aluminium-nickel alloy (CuAlNi), iron-nickel-aluminium alloy (FeNiAl) and combinations thereof. Particularly preferred is a shape memory alloy made of Nitinol (NiTi shape memory alloy). The Nitinol may be further an elastic, preferably superelastic, Nitinol, in particular in an untreated (as drawn, cold worked) state or partially annealed state. Especially preferred, the yarns made of shape memory material are Nitinol wires, in particular superelastic Nitinol wires.

The yarns made of the shape memory material (without the polymer sheathing) may have a thickness of 20 to 250 µm, preferably <125 µm, particularly preferred 25 to 100 µm. The sheathed shape memory material yarns may have a thickness of 30 to 300 µm, in particular 30 to 125 µm. Typically, single polymer yarns have a thickness in the range of 5 to 50 µm, in particular 10 to 20 µm.

Basically, the polymer sheathing may be formed from a polymer material differing from the material of the polymer yarns. However, preferred is a polymer sheathing made of the same polymer material as the polymer yarns. The polymer yarns are preferably free of any sheathing, in particular polymer sheathing. The polymer sheathing and/or the polymer yarns may be formed from a polymer material selected from the group consisting of polyesters such as poly(ethylene terephthalate) and poly(butylene terephthalate), polyethylene, poly(tetrafluoroethylene), including expanded poly(tetrafluoroethylene), poly(vinylidene fluoride), polypropylene, fluorinated ethylene propylene copolymer, polyvinyl acetate, polystyrene, polyether ketones, polyether ether ketones, polysulfides, polyaramides, polyacrylonitriles, naphthalene dicarboxylate derivates, such as polyethylene naphthalate, polybutylene naphthalate, poly-trimethylene naphthalate and polytrimethylenediol naphthalate, polyurethane, polyurea, silicon rubbers, polyamides, polycarbonates, polyaldehydes, natural rubbers, polyester copolymers, styrene-butadien copolymers, polyethers, such as fully or partly halogenated polyethers, copolymers and combinations thereof. Poly(ethylene terephthalate), copolymers thereof or combinations thereof are particularly preferred. The term "copolymers" as used herein relates to polymers which are composed of two or more different monomer units.

The yarns of the medical device may be in general textured, non-textured, shrunk and/or non-shrunk. For instance, the medical device may comprise textured and/or non-textured (smooth) polymer yarns, preferably textured and non-textured (smooth) polymer yarns. Furthermore, the polymer yarns may have a linear mass density of 0.1 to 220 dtex, in particular 30 to 110 dtex.

The device is preferably arranged in the form of a textile device, in particular textile implant. As used herein, the term "textile" and its variants refer to a structure of interlocked or interlaced yarns formed by weaving, knitting, braiding or the like. Accordingly, suitable textile constructions are, in particular, knitted fabrics, tricot fabrics, woven fabrics, non-woven fabrics, or spunlaid non-wovens. Particularly preferred is a device in the form of a knitted fabric or a woven fabric, in particular a woven fabric. The sheathed shape memory material yarns and the polymer yarns may be arranged in a textile pattern. Useful yarn patterns include textile patterns such as a braided pattern, a woven pattern, a knitted pattern, a filament wound pattern or combinations thereof. Desirably, the pattern is a woven textile pattern. More preferably, the yarns of the device are arranged in a common textile weave. Preferred is a textile weave selected from the group consisting of plain weave, warp twill weave, weft twill weave, broad rib twill weave, multiple rib twill weave, satin weave, warp satin weave, weft satin weave, and combinations thereof. With a device in the form of a woven fabric, the sheathed shape memory material yarns and/or the polymer yarns may be arranged in the warp direction and/or weft direction. For instance, the medical device is designed as a woven fabric, in particular a hollow tubular woven fabric, wherein the sheathed shape memory material yarns are arranged in the weft direction and the polymer yarns are arranged in the warp direction of the fabric. A further preferred device is designed as a woven fabric, in particular hollow tubular woven fabric, wherein the sheathed shape memory material yarns are arranged in the weft direction and textured and non-textured polymer yarns are alternately arranged in the warp direction of the fabric.

The device, in particular yarns thereof, may have a textured or structured surface, preferably on the outer surface thereof, including structures to allow engagement, in particular, of somatic cells. This allows an anchoring or securing of the device in a surrounding tissue region. The device may have in particular at least one of floats, linings, velour loops, textured yarns, and piles. In case of floats, the floats may extend over or under less than five subsequent yarns of the medical device.

Particular preference is given to a medical device formed as a hollow tubular device, in particular a hollow tubular fabric, preferably a hollow tubular woven fabric. In principal, the medical device may be selected from the group consisting of vascular grafts, balloon catheters, endoluminal prostheses, endoluminal grafts, stents and stent grafts. Preferably, the device is designed as an indwelling, particularly intraluminally pushable and placeable, device. As used herein, the term "intraluminally" and its variants refer to within a body lumen. Such placement is typically performed by non-invasive or minimally invasive procedures. In other words, such devices are intraluminally or intratubally placeable through percutaneous or orificial means into a body lumen of a patient. Moreover, as used herein, the phrase "body lumen" and its variants refer to a blood vessel, a bodily organ, or a bodily tube, like esophagus, trachea, duodenum, colon, and other parts of the digestive system, as well as urinary system and ureters, for example. Accordingly it is especially preferred that the medical device is selected from the group consisting of stents, endoluminal prostheses, endoluminal grafts and stent grafts.

Particularly preferably, the device is designed as a stent, in particular a textile stent, preferably a woven stent. Typical fields of application of a stent are hollow bodies or hollow organs in a vascular, gastrointestinal, tracheo-bronchial and/or urethral region. For instance, by application of a stent, malignant or benign obstructions, stenoses, aneurysms and lesions may be treated in the hollow bodies or hollow organs. Furthermore, the device may be a stent graft. Especially preferred, the device is designed as a graft, in particular as an endoluminal graft, preferably for the manufacture or production of a stent graft.

Further, the medical device may also have a bifurcation. Advantageously, the bifurcation allows the treatment of pathologically affected zones of hollow organs having a corresponding bifurcation. For instance, aneurysms located at the transition from abdominal aorta to pelvic arteries may be treated by a bifurcated device.

The device may have a water permeability of 40 to 2000 ml/(min·cm)$^2$, preferably 50 to 800 ml/(min·cm)$^2$. The device may have a thickness, in particular a wall thickness, of 60 to 400 μm, preferably of 100 to 250 μm, particularly preferred of a maximum of 150 μm. Due to a small thickness, particularly wall thickness, the device may be delivered to a treatment zone using commercially available delivery devices, in particular trocars or catheters, and may be placed in situ using typical release systems, without any inconveniences which might occur due to an extensive thickness or wall thickness, in practical application.

The medical device is preferably designed as a drug eluting device or a drug delivery device. In particular, the device, for instance the polymer sheathing and/or the polymer yarns, contains a drug or a bio-therapeutic agent such as thrombo-resistant agents, antibiotic agents, anti-viral agents, anti-inflammatory agents, analgesic agents, hemostatic agents, anti-proliferating agents, anti-tumor agents, cell cycle regulating agents, cell differentiating agents, cell recruiting agents, cell growth stimulating agents, derivatives thereof, fragments thereof, pharmaceutical salts thereof, or combinations thereof.

Useful thrombo-resistant agents may include, for example, heparin, heparin sulphate, hirudin, chondroitin sulphate, dermatan sulphate, keratin sulphate, lytic agents, including urokinase and streptokinase, their homologs, analogs, fragments, derivatives and pharmaceutical salts thereof.

Useful antibiotics may include, for example, penicillins, cephalosporins, vancomy-cins, aminoglycosides, quinolones, polymyxins, erythromycins, tetracyclines, chloramphenicols, clindamycins, lincomycins, sulphonamides, their homologs, analogs, fragments, derivatives, pharmaceutical salts and mixtures thereof.

Useful anti-tumor agents may include, for example, paclitaxel, docetaxel, alkylating agents including mechlorethamine, chlorambucil, cyclophosphamide, melphalan and ifosfamide; antimetabolites including methotrexate, 6-mercaptopurine, 5-fluorouracil and cytarabine; plant alkaloids including vinblastine, vincristine and etoposide; antibiotics including doxorubicin, daunomycin, bleomycin, and mitomycin; nitrosureas including carmustine and lomustine; inorganic ions including cisplatin; biological response modifiers including interferon; enzymes including asparaginase; and hormones including tamoxifen and flutamide; their homologs, analogs, fragments, derivatives, pharmaceutical salts and mixtures thereof.

Useful anti-viral agents may include, for example, amantadines, rimantadines, ribavirins, idoxuridines, vidarabines, trifluridines, acyclovirs, ganciclovirs, zidovudines, foscarnets, interferons, their homologs, analogs, fragments, derivatives, pharmaceutical salts and mixtures thereof.

Further, the device may contain a sealant composition to fix the device at a desired treatment site, preferably intraluminal treatment site.

Further, the device may be coated with a coating, in particular a bio-absorbable coating such as collagen, albumin, elastin, polysaccharides and the like. In particular, the coating may be formed as a hydrogel or solgel. Furthermore, the coating may contain the above-described drugs and biotherapeutic agents or any combination thereof.

The device may also include a radiopaque guideline or marker to provide means for viewing the device fluoroscopically within a body lumen. The marker may extend the length of the device. Other patterns for markers may also be employed. Radiopaque markers assist the physician to visualize the device both during and after an implantation. The marker helps to show the physician that the device is properly positioned.

We also provide a delivery system comprising a medical device as well as a delivery instrument, preferably a trocar or a catheter, to insert the device into a human or animal hollow body by the delivery instrument. Additionally, the delivery system may comprise suitable releasing systems to facilitate deployment of the device at a desired site within the body lumen. In relation to further features and details, in particular concerning the device, reference is made to the above and the following description in its entirety.

Furthermore, we provide a method for the production of a medical device, wherein a device comprising yarns made of a shape memory material and polymer yarns is subject to a thermal shape-setting treatment, preferably a low temperature shape setting treatment. Preferably, the yarns made of the shape memory material comprise a polymer sheathing (sheathed shape memory material yarns).

Usually, the device to be subject to a thermal shape-setting is provided in a thermally untreated form. Before the thermal shape-setting treatment, the device is usually produced as a textile device using or processing sheathed shape memory material yarns and polymer yarns. The device may be provided in the form of a tube-type or hose-type device, in particular a tubular fabric, preferably in the form of a stent or stent graft material, prior to the thermal shape setting.

Preferably, the device is subject to thermal shape setting in a stretched condition. To this means, the device may be positioned on a mandrel, in particular a metal cylinder, for thermal shape setting.

A particular preference is given to the use of a shape memory alloy as the shape memory material. The device to be shape set, as mentioned above, is preferably stretched on a mandrel. The thermal shape setting is particularly performed at an environmental temperature≤500° C. (at or above which conventional heat treatment of Nitinol shape memory alloy is commonly performed). Preferably the thermal shape setting is performed at a temperature≤250° C. and in particular >100° C. The thermal shape setting may be performed particularly in a temperature range of 150 to 250° C., preferably 170 to 210° C.

The thermal shape setting may be performed during a period of 10 min to 10 h, preferably 30 min to 5 h. Generally, the thermal shape setting of the device may be performed in an adequate furnace.

Furthermore, mechanical force in the sheathed shape memory material yarns may be preset or maintained while the thermal shape setting of the device is being performed. The device may be subjected to ultrasonic excitation while the thermal shape setting of the device is being performed. The sheathed shape memory material yarns may also be subjected to pulsed DC electric current excitation while the thermal shape setting of the device is being performed.

We further provide a medical device obtained or obtainable by our method. In relation to further features and details, reference is made to the previous disclosure in its entirety.

We still further provide a method using our medical device, comprising percutaneously or orificially placing the device within a body lumen. In relation to further features and details, reference is made to the previous disclosure in its entirety.

In a final aspect, we also provide for the use of yarns made of a shape memory material, the yarns being preferably sheathed by a polymer, and polymer yarns for the production or manufacture of our device, in particular a stent, stent graft or graft, preferably for the production or manufacture of a stent graft. In relation to further features and details, reference is made to the previous disclosure in its entirety.

In summary, we provide a medical device, preferably in the form of a stent, stent graft or even more preferred in the form a stent graft material, characterized by the particular advantage of an increased displacement resistance among the yarns made of shape memory material, the yarns being preferably sheathed by a polymer, and the polymer yarns, whereby the occurrence of potential irritation and leakage zones will be prevented. Furthermore, the device is characterized by the particular advantage of a smooth internal wall to obviate the formation of thromboses, and thus prevent a risk of restenoses occurring, for example. The preferred thin-walled design of the device allows also placing the device within a body lumen without excessive inconveniences using typical insertion devices and delivery instruments. Another advantage is that the device may be subject to thermal shape setting at significantly lower temperatures and thus allowing for a production under more gentle conditions as compared to conventional devices, in particular stents or stent grafts, and without affecting the restoration forces required for deployment of the device within a body lumen.

In the following, our disclosure will be illustrated in more detail by a disclosure of preferred examples. In the examples, individual features may be realized exclusively or in combination with other features. Any described example is given for the sole purpose of illustration and better understanding and is in no way to be interpreted as a limitation.

Example 1

Figure 3:
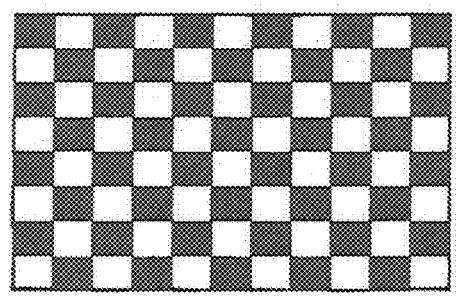
FIG. 3 is a schematic representation of one example of a woven fabric weave pattern.

A hollow tubular woven fabric whose weave pattern is displayed in FIG. 3 is provided. The fabric consists of 600 polyester yarns (100f80) and of a Nitinol wire (diameter 50 μm) that is sheathed by a polyester yarn. The polyester yarns are arranged in the warp direction and the sheathed Nitinol wire is arranged in the weft direction of the fabric. In FIG. 3, the polyester yarns are displayed as white squares and the sheathed Nitinol wire is displayed as black squares. For production of a medical device, the fabric is stretched on a mandrel having a diameter of 30 mm and is subsequent thermally shape set at a temperature of 180° C. The wall thickness of the resulting fabric ranges between 180 and 200 μm.

Example 2

A hollow tubular woven fabric whose weave pattern is displayed in FIG. 3 is provided. The fabric consists of 300 untextured (smooth) polyester yarns (100f80), 300 textured polyester yarns (100f80) and of a Nitinol wire (diameter 30 µm) that is sheathed by a polyester yarn. The untextured polyester yarns and textured polyester yarns are alternately arranged in the warp direction of the fabric. The sheathed Nitinol wire is arranged in the weft direction of the fabric. The fabric is designed in a plain weave. In FIG. 3, the untextured (smooth) polyester yarns are displayed as white squares, the textured polyester yarns are displayed as white squares and the Nitinol wire is displayed as black squares. For the production of a medical device, the fabric is stretched on a mandrel having a diameter of 30 mm and is subsequent thermally shape set at a temperature of 180° C. The wall thickness of the resulting fabric ranges between 170 and 180 µm.

Example 3

Figure 4:
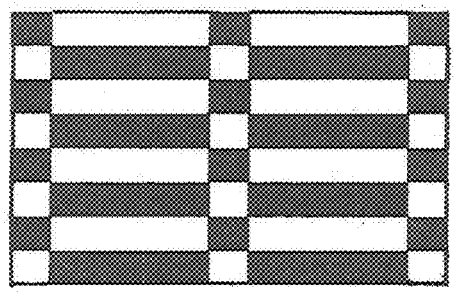
FIG. 4 is a schematic representation of another example of a woven fabric weave pattern.

A hollow tubular woven fabric whose weave pattern is displayed in FIG. 4 is provided. The woven fabric consists of 840 polyester yarns (50f40) and of a Nitinol wire (diameter 30 µm) that is sheathed by a polyester yarn. The polyester yarns are arranged in the warp direction and the sheathed Nitinol wire is arranged in the weft direction of the fabric. The fabric is designed in a modified plain weave wherein the sheathed Nitinol wire is designed as a float. With respect to adjacent weft rows of the fabric, the sheathed Nitinol wire has an alternate float configuration. In one weft row, the sheathed Nitinol wire floats over four polymer yarns and then crosses under one polyester yarn. In the next weft row, the sheathed Nitinol wire crosses under four polymer yarns and then floats over one polyester yarn or the like. In FIG. 4, the polymer yarns are displayed as white squares, the sheathed Nitinol wire is displayed as black squares and the floats are displayed as black rectangles (covering the surface of four black squares). For the production of a medical device, the fabric is stretched on a mandrel having a diameter of 30 mm and is subsequent thermally shape set at a temperature of 190° C. The wall thickness of the resulting fabric ranges between 100 and 120 µm.

Example 4

A hollow tubular woven fabric whose weave pattern is displayed in FIG. 3 is provided. The fabric consists of 840 polyester yarns (42f40) and of a Nitinol wire (diameter 30 µm) that is sheathed by a polyester yarn. The polyester yarns are arranged in the warp direction and the sheathed Nitinol wire is arranged in the weft direction of the fabric. The fabric is designed in a plain weave. For the production of a medical device, the fabric is stretched on a mandrel having a diameter of about 8 mm and is subsequent thermally shape set at a temperature of 190° C. The wall thickness of the resulting fabric ranges between 90 and 110 µm.

Example 5

A hollow tubular woven fabric whose weave pattern is displayed in FIG. 3 is provided. The fabric consists of 400 untextured (smooth) polyester yarns (100f80) and of 200 Nitinol wires (diameter 30 µm) that are sheathed by a polyester yarn. With respect to the weft direction of the fabric, untextured (smooth) polyester yarns and sheathed Nitinol wires are processed in an alternate fashion. With respect to the warp direction of the fabric, only the sheathed Nitinol wires are processed. The woven fabric is designed in a plain weave. In FIG. 3, the polymer yarns are displayed as white and as black squares. For the production of a medical device, the fabric is stretched on a mandrel having a diameter of about 30 mm and is subsequent thermally shape set at a temperature of 190° C. The wall thickness of the resulting fabric ranges between 200 and 220 µm.

Example 6

A hollow tubular woven fabric whose weave pattern is displayed in FIG. 3 is provided. The fabric consists of 600 polyester yarns (100f80) and of a Nitinol wire (diameter 100 µm) that is sheathed by a polyester yarn. The polyester yarns are arranged in the warp direction and the sheathed Nitinol wire is arranged in the weft direction of the fabric. The fabric is designed in a plain weave. For the production of a medical device, the fabric is stretched on a mandrel having a diameter of 30 mm and is subsequent thermally shape set at a temperature of 210° C. The wall thickness of the resulting fabric ranges between 260 and 300 µm.

Example 7

Figure 5:
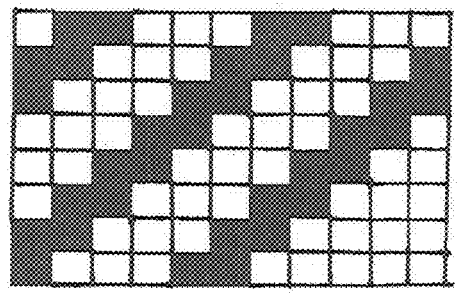
FIG. 5 is a schematic representation of yet another example of a woven fabric weave pattern.

A hollow tubular woven fabric whose weave pattern is displayed in FIG. 5 is provided. The fabric consists of 600 polyester yarns (100f80) and of a Nitinol wire (diameter 50 µm) that is sheathed by a polyester yarn. The polyester yarns are arranged in the warp direction and the sheathed Nitinol wire is arranged in the weft direction of the fabric. The fabric is designed in a twill weave. In FIG. 5, the polymer yarns are displayed as white squares and the sheathed Nitinol wire is displayed as black squares. For the manufacture of a medical device, the fabric is stretched on a mandrel having a diameter of 30 mm and is subsequent thermally shape set at a temperature of 180° C. The wall thickness of the resulting fabric ranges between 180 to 200 µm.

The invention claimed is:

1. A medical device comprising a hollow tubular woven fabric consisting of yarns made of a low temperature shape set shape memory metal or low temperature shape set shape memory alloy and consisting of polymer yarns, wherein the yarns made of said low temperature shape set shape metal or alloy comprise a textile sheathing, the sheathed shape memory metal or alloy yarns are arranged in a weft direction of the woven fabric, the polymer yarns are arranged in a warp direction of the woven fabric, wherein in the woven fabric, both the low temperature shape set memory metal or low temperature shape set memory alloy and the polymer yarns are in a thermally set condition.

2. The medical device according to claim 1, wherein the textile sheathing is in the form of monofilaments, multifilaments or a combination thereof.

3. The medical device according to claim 1, wherein said textile sheathing enwinds, wraps or is plait around the yarns made of said low temperature shape set shape memory metal or alloy.

4. The medical device according to claim 1, wherein the yarns made of said low temperature shape set shape memory metal or alloy and the textile sheathing are yarns having a core-sheath structure, wherein the core is formed by said yarns made of said low temperature shape set shape memory material and the sheath is formed by said textile sheathing.

5. The medical device according to claim 1, wherein the sheathed shape memory metal or alloy yarns have a Young's modulus of 20 to 80 N/mm$^2$.

6. The medical device according to claim 1, wherein the polymer yarns have a Young's modulus of 300 to 1500 cN/tex.

7. The medical device according to claim 1, wherein the device has a radial expansive pressure of 0.2 to 30 kPa.

8. The medical device according to claim 1, wherein the textile sheathing has a proportion of 10 to 90% by weight, based on the total weight of the sheathed shape memory material yarns.

9. The medical device according to claim 1, wherein the yarns made of said low temperature shape set shape memory metal or alloy, without said textile sheathing, have a thickness of 20 to 250 µm.

10. The medical device according to claim 1, wherein the textile sheathing is made of the same material as the polymer yarns.

11. The medical device according to claim 1, wherein the textile sheathing, the polymer yarns or a combination thereof are formed from a polymer material selected from the group consisting of polyesters, polyethylene, poly(tetrafluoroethylene), poly(vinylidene fluoride), polypropylene, fluorinated ethylene propylene copolymer, polyvinyl acetate, polystyrene, polyether ketones, polyether ether ketones, polysulphides, polyaramides, polyacrylonitriles, naphthalene dicarboxylate derivates, polyurethane, polyurea, silicon rubbers, polyamides, polycarbonates, polyaldehydes, natural rubbers, polyester copolymers, styrene-butadiene copolymers, polyethers, copolymers and combinations thereof.

12. The medical device according to claim 11, wherein the polyester is poly(ethylene terephthalate).

13. The medical device according to claim 1, wherein the polymer yarns have a linear mass density of 0.1 to 220 dtex.

14. The medical device according to claim 1, wherein the device is a knitted or woven textile device.

15. The medical device according to claim 1, wherein the sheathed shape memory metal or alloy yarns and the polymer yarns are arranged in a textile weave.

16. The medical device according to claim 15, wherein the textile weave is selected from the group consisting of plain weave, warp twill weave, weft twill weave, broad rib twill weave, multiple rib twill weave, warp satin weave, and weft satin weave.

17. The medical device according to claim 1, wherein the device is arranged in the form of a textile device having a structured surface which is at least one of floats, linings, velour loops, textured yarns, and piles.

18. The medical device according to claim 1, which is a hollow tubular device.

19. The medical device according to claim 1, wherein the device is an indwelling intraluminally placeable device.

20. The medical device according to claim 1, wherein the device is an endoluminal graft for the production of a stent graft.

21. The medical device according to claim 1, wherein the device has a bifurcation.

22. The medical device according to claim 1, wherein the device has water permeability of 40 to 2000 ml/(min·cm)$^2$.

23. The medical device according to claim 1, wherein the device has a wall thickness of 60 to 400 µm.

24. A delivery system comprising a medical device according to claim 1 and a delivery instrument.

25. A method of producing the medical device according to claim 1, comprising subjecting the medical device to a thermal shape setting procedure.

26. The method according to claim 25, wherein the device is produced as a textile device using sheathed shape memory metal or alloy yarns and polymer yarns prior to the thermal shape setting.

27. The method according to claim 25, wherein the medical device is a tube or hose device prior to said thermal shape setting.

28. The method according to claim 25, wherein the device is subject to thermal shape setting in a stretched condition.

29. The method according to claim 25, wherein the device is positioned on a mandrel for thermal shape setting.

30. The method according to claim 25, wherein the thermal shape setting is performed at a temperature ≤250° C.

31. The method according to claim 25, wherein the thermal shape setting is performed for a period of 10 min to 10 h.

32. A method of using a medical device according to claim 1, comprising percutaneously or orificially placing the device within a body lumen.

33. A medical device comprising a hollow tubular woven fabric consisting of yarns made of a low temperature shape set shape memory metal or low temperature shape set memory alloy and consisting of polymer yarns, wherein the yarns made of said low temperature shape set shape memory metal or alloy comprise a textile sheathing, the sheathed shape memory metal or alloy yarns are arranged in a warp direction of the woven fabric, the polymer yarns are arranged in a weft direction of the woven fabric, wherein in the woven fabric, both the low temperature shape set memory metal or low temperature shape set memory alloy and the polymer yarns are in a thermally set condition.

* * * * *